United States Patent [19]
Chein et al.

[11] Patent Number: 5,800,598
[45] Date of Patent: Sep. 1, 1998

[54] GENERATOR FOR PRODUCING A NARROWLY SIZE-DISTRIBUTED AEROSOL

[75] Inventors: Hung-Min Chein, Hsinchu; Charles C. K. Chou, Taoyuan Hsien, both of Taiwan

[73] Assignee: Industrial Technology Research Institute, Taiwan

[21] Appl. No.: 763,786

[22] Filed: Dec. 11, 1996

[30] Foreign Application Priority Data

Jun. 28, 1996 [TW] Taiwan ................................. 85209827

[51] Int. Cl.$^6$ ........................................... B01D 19/00
[52] U.S. Cl. ........................... 96/190; 96/360; 96/361; 55/318
[58] Field of Search ........................ 55/226, 257.1, 55/257.5, 259, 318, 340, 342, 423, 431, 462, 466, 468, DIG. 14, DIG. 23; 95/185, 186, 198, 243, 268; 96/181, 190, 203, 215, 219, 360, 361

[56] References Cited

U.S. PATENT DOCUMENTS

| | | | |
|---|---|---|---|
| 2,785,768 | 3/1957 | Gauchard | 55/257.5 |
| 2,869,188 | 1/1959 | Cameto | 55/257.5 |
| 3,302,374 | 2/1967 | Szekely | 55/257.5 |
| 3,385,030 | 5/1968 | Letvin | 55/257.5 |
| 3,725,271 | 4/1973 | Giannotti | 55/DIG. 14 |
| 4,340,474 | 7/1982 | Johnston | 55/DIG. 14 |
| 5,277,707 | 1/1994 | Munk et al. | 55/226 |

FOREIGN PATENT DOCUMENTS

416390  7/1925  Germany .............. 55/DIG. 14

*Primary Examiner*—C. Scott Bushey
*Attorney, Agent, or Firm*—Birch, Stewart, Kolasch & Birch, LLP

[57] ABSTRACT

According to a generator for producing a narrowly size-distributed aerosol, the solution is atomized into the first droplets including a predetermined small-sized range of droplets by the atomizer, and then using the droplet depositor, the larger droplets from the predetermined small-sized range of droplets are deposited in the first droplets, and wherein the second droplets are formed from the first droplets, and then a particulate screening and separating device is used to extract the third droplets smaller than the predetermined small-sized range of droplets within the second droplets, and the predetermined small-sized range of droplets can be obtained thereof. Therefore, a aerosol generator can function as a device characterized with the alternative distributions of a narrowly size-distributed aerosol with high concentration in mass, and the liquid or solid aerosol can be generated thereof. The Geometric Standard Deviation (GSD) of the droplet size distribution can be kept under 1.5 and the Mass Median Aerodynamic Diameter (MMAD) is selective so that the user alters the concentration of the solvent from the solution before atomizing. Also, this generator can be continuously operated for 8 hours by the self-purification system. The relative GSD with respect to the MMAD, GSD and the Aerosol Generation Rate (AGR) can be maintained under 10% for 8 hours.

17 Claims, 5 Drawing Sheets

FIG. 5

GENERATOR FOR PRODUCING A NARROWLY SIZE-DISTRIBUTED AEROSOL

BACKGROUND OF THE INVENTION

1. Field of the Invention

The present invention generally relates to a generator for producing a narrowly size-distributed aerosol. More particular, the present invention relates to the aerosol generator characterized by the alternative distribution of the narrowly size-distributed aerosol with a high concentration of mass.

2. Description of the Related Art

In the study of aerosols, the production of narrowly size-distributed aerosols characterized by the alternative distributions of the narrowly size-distributed aerosols with a high concentration of mass is a current topic. In particular, the exposure research on human or animal and the testing aspects of high-efficiency filters are both indispensable to this field. In general, the aerosol can be considered to have a narrow-sized distribution when the GSD (Geometric Standard Deviation) of the aerosol is in the range of 1.0 to 1.5. If the GSD of the aerosol is above 2.0, this aerosol is considered to have a extensive-sized distribution. Idealistically, the aerosol with a monodisperse, i.e., GSD= 1.0, is the best testing aerosol. But, with all the present skills of the generator for producing the monodisperse aerosol, the density of the testing aerosol is too low to meet the requirements of aerosols with high concentration. Furthermore, the generator for producing the polydisperse aerosol can generate enough aerosol in production, but the value of GSD of the aerosol usually is above 2.0 and it does not fit to the exposure research and filter paper testing.

The size of the aerosol plays an important role in evaluating the inhalation of particulate detrimental to the human respiratory tract. The location of the sedimentary particulate in the human respiratory tract fully depends on the size of the particulate; that is, the sediment of the particulate is in proportion to the density of the aerosol. Both the size and mass of the aerosol are two factors that principally endanger the human respiratory tract. Testing penetrability on high-efficiency filter paper is necessary for a range of some aerosol particulate sizes. On the one hand, the penetrability of the filter paper depends on the different sizes of aerosol. On the other, testing that uses the monodisperse aerosol as a sample is time consuming and expensive. Furthermore, polydisperse aerosols are not suitable for filter paper testing because the size of the aerosol concentrate in the region is less than 1 micron (<1 μm). Therefore, when the testing is applied to coarse particulates, the deviation of results markedly increases.

SUMMARY OF THE INVENTION

To attain the above object, the present invention provides a generator for producing a narrowly size-distributed aerosol. The generator, which uses a reservoir for storing the solution and a gas resource to form the predetermined small-sized range of droplets from said reservoir, comprises:

an atomizer connected to the reservoir, wherein the atomizer atomizes the solution by the gas generator and forms the first droplets including the predetermined small-sized range of droplet;

a droplet depositor provided with an outlet and an inlet installed with the atomizer, wherein the droplet depositor deposits the larger droplets from the predetermined small-sized range of droplets in the first droplets, and wherein the second droplets are formed from the first droplets and passed out through the outlet of the droplet depositor; and a particulate screening and separating means installed on the outlet of the droplet depositor, wherein the particulate screening and separating means is used to extract the third droplets smaller than the predetermined small-sized range of droplet within the second droplets, thereby obtaining the predetermined small-sized range of droplet.

The particulate screening and separating means comprises:

a cylindrical body provided with a first opening and a second opening, wherein said first opening is connected to said outlet of said droplet depositor for conducting said second droplets therein;

a jet nozzle mounted in said first opening of said cylindrical body for accelerating said second droplets and a nozzle orifice provided thereon; and a collecting pipe installed in said first opening of said cylindrical body and a collecting opening provided thereon, wherein said collecting opening spaced by a preset distance opposite to said nozzle orifice of said jet nozzle is used to collect said predetermined small-sized range of droplet, and said second opening of said cylindrical body is used to conduct said third droplets.

Accordingly, it is an object of this invention to provide an alternative distribution of the narrowly size-distributed aerosol with a high concentration of mass.

It is a further purpose of this invention to generate a liquid or solid aerosol.

A still further purpose of this invention is to obtain the Mass Median Aerodynamic Diameter (MMAD) by altering the concentration of the solvent from the solution before atomizing.

Another purpose of this invention is to keep the Geometric Standard Deviation (GSD) of the droplet size distribution under 1.5.

Another purpose of the present invention is to keep the relative standard deviation of the GSD, MMAD, and the AGR under 10% by continuous operation of the self-purification system for 8 hours.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

Other objects, features and advantages of the present invention will become apparent by way of the following detailed description of the preferred but non-limiting embodiment. The description is made with reference to the accompanying drawings, wherein:

FIG. 5 illustrates a particulate size distribution graph in which water solution of the uranine in 0.01% (volume percentage) has been volatilized and dried and the solid particulate of the uranine generated thereof and plotted according to the present invention.

DESCRIPTION OF THE PREFERRED EMBODIMENTS

Figure 1:
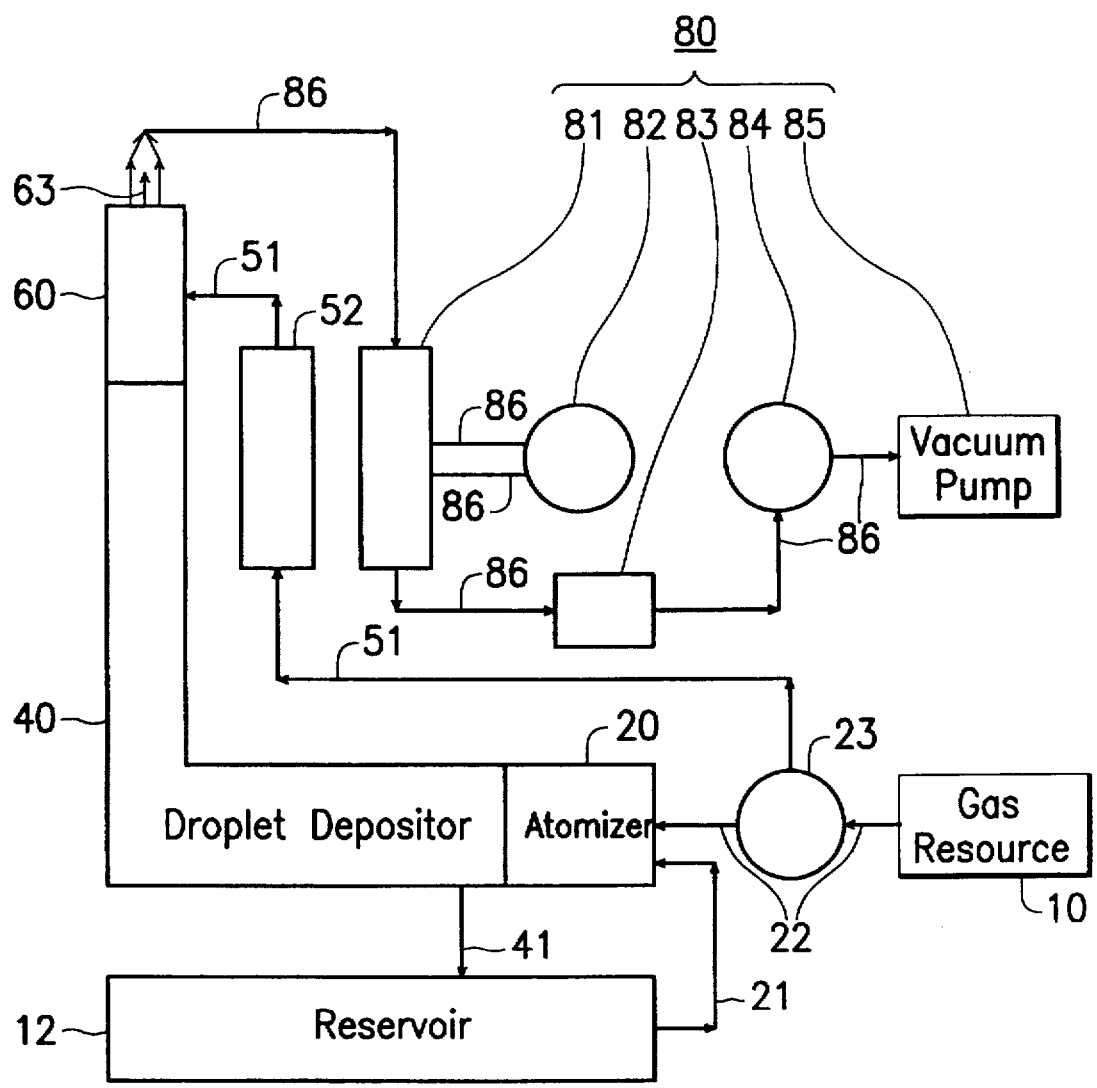
FIG. 1 is a schematic view showing the generator for producing a narrowly size-distributed aerosol according to the present invention.
Figure 2:
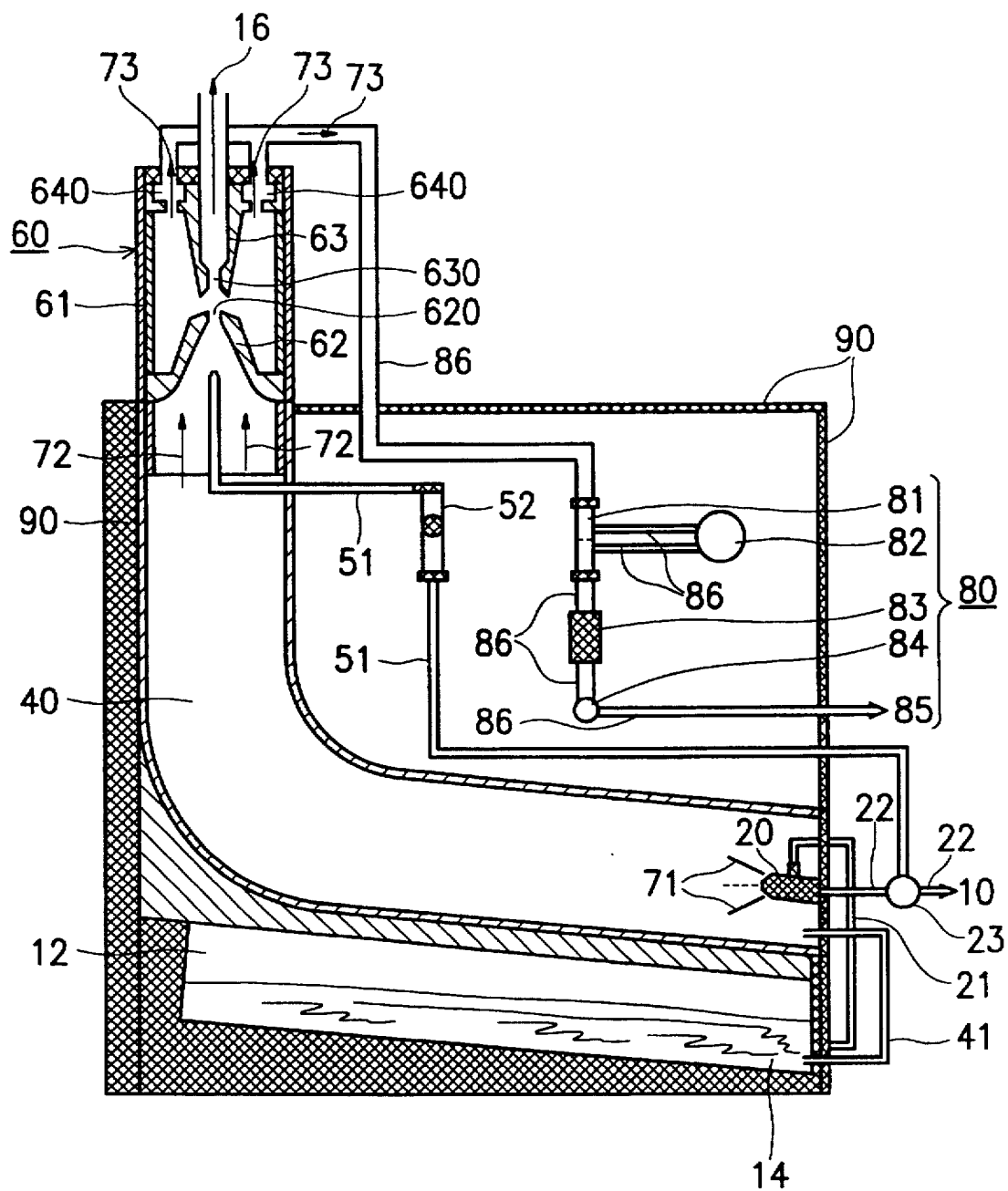
FIG. 2 is a cross-sectional view showing the generator for producing a narrowly size-distributed aerosol according to the present invention.

Referring now to the drawings and particularly to FIG. 1 and FIG. 2, a generator for producing a narrowly size-distributed aerosol of the present invention relates to obtaining a predetermined small-sized range of droplets by means of using a gas resource 10 in coordination with the solution 14 contained within the reservoir 12. The generator mainly comprises an atomizer 20, a droplet depositor 40 and a particulate screening and separating means.

The atomizer 20 may utilize a nebulizing nozzle connected to the reservoir 12 by the pipe 21, wherein the pipe 22 connects the gas resource 10 to the atomizer 20. A pressure regulator 23 is mounted on the pipe 22 and controls the pressure and flow of the gas from the reservoir 10 to the atomizer 20. The clean high-pressure gas (air) stored in the reservoir 10 is fed into the atomizer 20 where a low-pressure venturi effect is generated and the solution 14 with constant flow is drawn from the reservoir 10 through the atomizer 20. At the same time that the centrifugal vortex motion in the atomizer 20 can atomize the solution 14 into the first droplets 71 characterized with a broad particulate size distribution and which therein includes the predetermined small-sized range droplet 16.

The droplet depositor 40 may be a diversion pipe formed with at least one bend thereon. In this preferred embodiment, there is provided a diversion pipe 40 which comprises an inlet and outlet, wherein the diversion pipe 40 is roughly L-shaped. The atomizer 20 is mounted on the inlet of the diversion pipe 40, and the L-shaped diversion pipe 40 is generally installed at 7 degrees with respect to the horizontal line from the inlet to the bend thereon. Therefore, when the first droplets 71 generated by the atomizer 20 have been sprayed into the L-shaped diversion pipe 40, some droplets which are larger than the predetermined small-sized range of droplet contained in the first droplets 71 are eliminated by the action of gravitational deposit and inertia impact, and these larger droplets are expelled by the inertia impact (centrifugal force) and remain in the L-shaped diversion pipe 40 when its passes through the bend thereon. The second droplets 72, therefore, are formed by the first droplets 72 and passed out through the outlet of the L-shaped diversion pipe 40. A return pipe 41 installed between the L-shaped diversion pipe 40 and the reservoir 12 is used to automatically conduct the solution remaining in the L-type diversion pipe 40 into the reservoir 12 for recycling. Solution consumption can be reduced up to 90% by implementing the return pipe, thereby lowering cost.

The particulate screening and separating means may be a virtual impactor mounted on the outlet of the diversion pipe 40. The particulate screening and separating means comprises a cylindrical body 61, a jet nozzle 62 and a collecting pipe 63. The cylindrical body 61 has a first opening and second opening. The first opening of the cylindrical body 61 is connected to the outlet of the diversion pipe 40 so as to conduct the second droplets 72 therein. The jet nozzle 62 includes a nozzle orifice 620 and is designed as a funnel in streamlined shape. The nozzle orifice 620 installed in the first opening of the cylindrical body 61 functions as an accelerator for speeding up the second droplets 72, and the shape of the nozzle orifice 620 is formed at a rake angle of 15 degrees (15°) so as to drip the solution therefrom. The collecting pipe 63 is mounted on the second opening of the cylindrical body 61 and a collecting orifice 630 is formed thereon. The collecting orifice 630 is opposite to the nozzle orifice 620 of the jet nozzle 62 at a preset distance therebetween, and a extracting orifice 640 is formed on the circumference of the second opening of the collecting pipe 63. The extracting orifice 640 is used to extract the third droplets 73 which are smaller than the predetermined small-sized range of droplet 16 within the second droplets 72. Since the mass and inertia of the predetermined small-sized range of droplets 16 are greater than the third droplets 72 during the extracting process, the predetermined small-sized range of droplets 16 are collected by the collecting pipe 63. According to a journal article by B. T. Chen, H. C. Yen and Y. S. Cheng in "Aerosol Science and Technology" (volume 5), wherein the separation of the particulate can meet the standard with respect to stability and completion as well as eliminate the particulate pollution simultaneously by maintaining the aerosol added therein around a purified air axial flow. In this preferred embodiment, therefore, the purification of the central axial flow can be generated whereby the pipe 51 conduct the clean air into the particulate screening and separating means 60. Further, a gas control flow means 52 can be installed in the pipe 51, wherein the gas control flow means 52 comprises a floating flow meter and a needle valve. The quantitative clean gas (air) is delivered from the pipe 51 to the particulate screening and separating means 60 the through the gas control flow means 52.

Moreover, the third droplets 73 also can be extracted from the particulate screening and separating means 60 by an air intake flow control device 80. The air intake flow control device 80 comprises a microporous flow meter 81, a pressure differential 82, a filter 83, a needle valve 84, a vacuum pump 85 and the pipes 86 connected to the extracting orifice 640 of the particulate screening and separating means 60. The pressure of the third droplets 73 in the pipes 86 is measured by the microporous flow meter 81 front and rear, and the present pressure value is transmitted to the pressure differential 82 for monitoring the flow. The vacuum pump 85 is used to pump the third droplets 73 from the extracting orifice 640 to the filter 83 through the pipe 86, and the needle valve 84 is used to adjust the air flow filtered from the needle valve 84.

The particulate screening and separating means 60 can be broken down into sub-assemblies and amalgamated into the assembly process. It is flexible that the extracted air flow from the means 60 can be filtered at any size of testing aerosol by the user. As shown in FIG. 2, the generator for producing a narrowly size-distributed aerosol according to the present invention can be assembled within a housing 90 with cubic dimensions of 100 cm×50 cm×100 cm.

Figure 3:
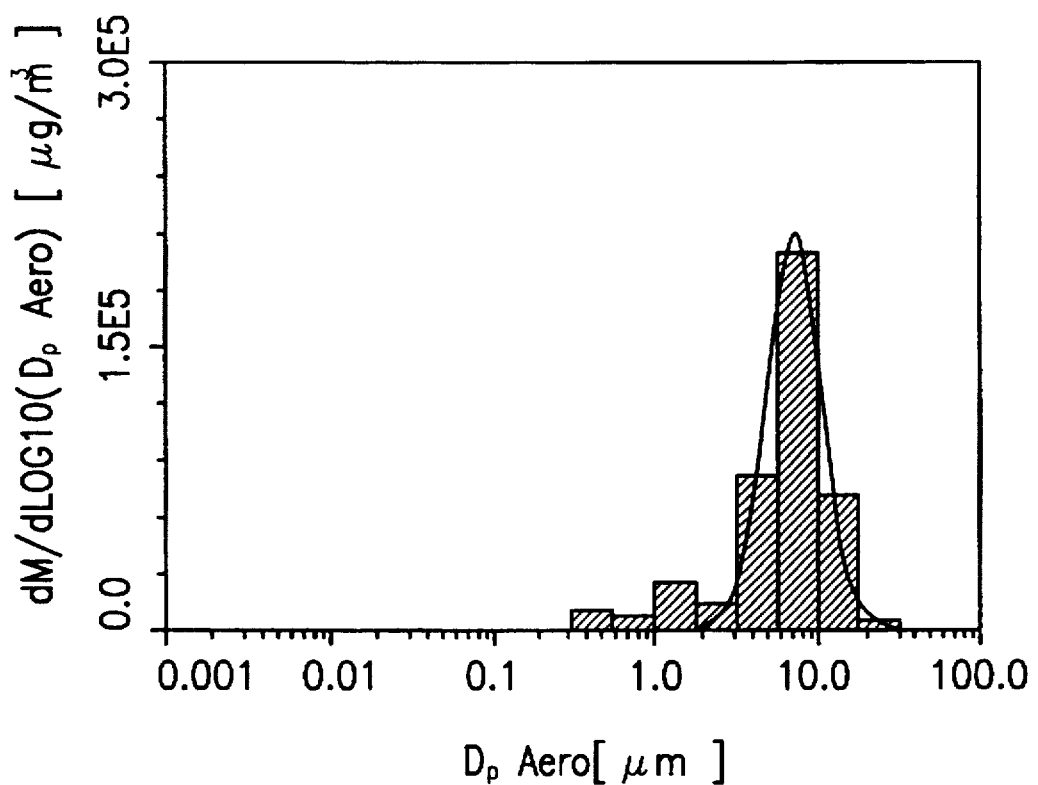
FIG. 3 illustrates a particulate size distribution graph in which the corn oil droplets have been generated by the generator for producing a narrowly size-distributed aerosol and plotted according to the present invention.

FIG. 3 illustrates a particulate size distribution graph in which the droplets of corn oil have been generated by the generator for producing a narrowly size-distributed aerosol and plotted according to the present invention. In this distribution, the MMAD of the corn oil droplets is 7.24 μm, and the GSD is 1.48, and the AGR is 15.31 mg/min.

Figure 4:
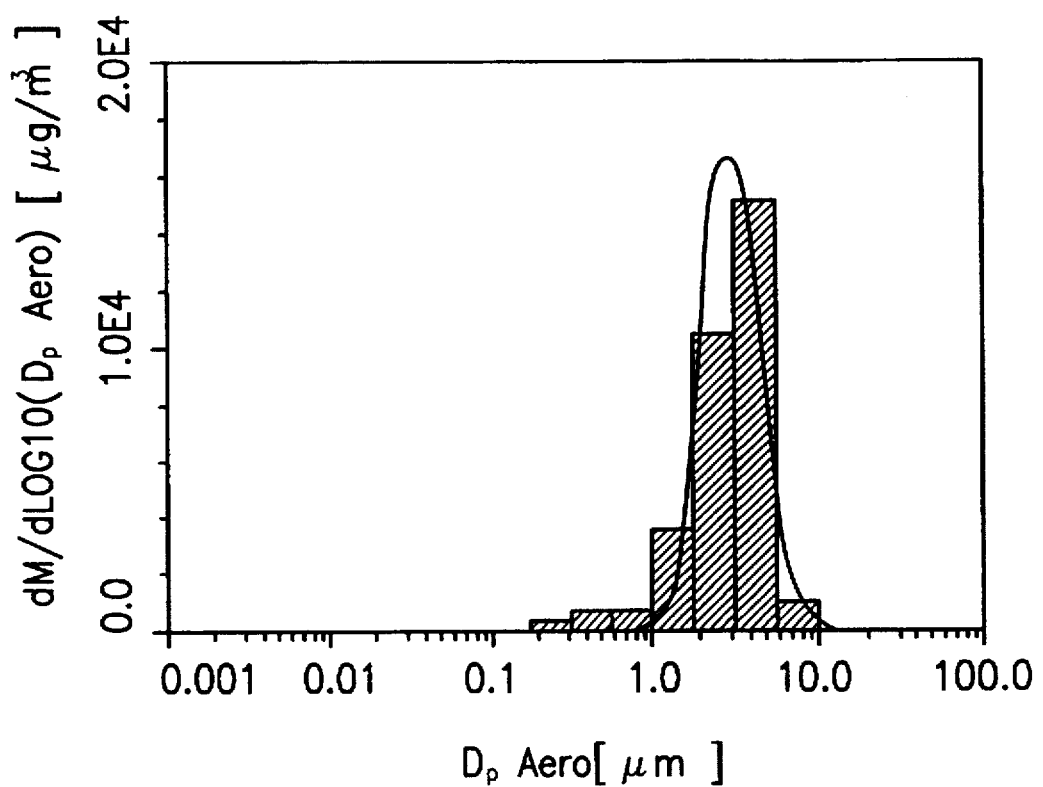
FIG. 4 illustrates a particulate size distribution graph in which the saline solution in 1% (volume percentage) has been volatilized and dried and the solid particulate of the kitchen-salt generated thereof and plotted according to the present invention.

FIG. 4 illustrates a particulate size distribution graph in which the saline solution in 1% (volume percentage) has been volatilized and dried, and the kitchen-salt solid particulate generated thereof and plotted according to the present invention. In this distribution, the MMAD of the oil droplet of the kitchen-salt solid particulate is 3.08 µm, and the GSD is 1.47, and the AGR is 2.35 mg/min.

Figure 5:
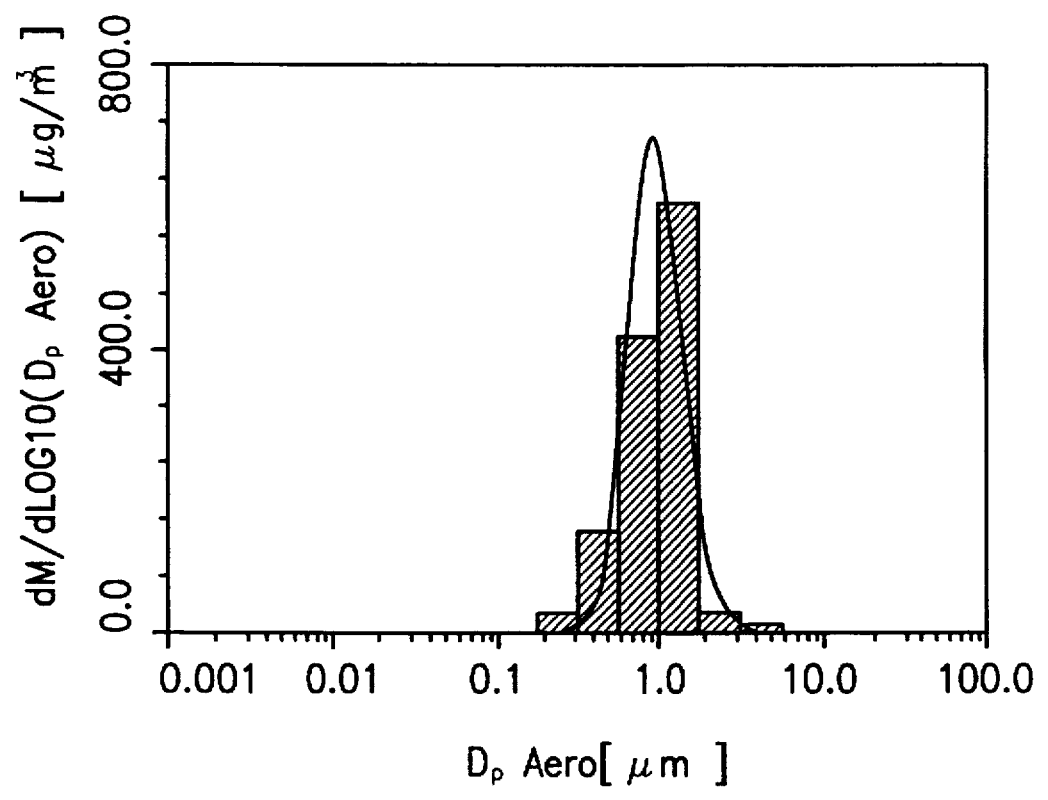

FIG. 5 illustrates a particulate size distribution graph in which water solution of the uranine in 0.01% (volume percentage) has been volatilized and dried and the uranine solid particulate generated thereof and plotted according to the present invention. In this distribution, the MMAD of the solid particulate of the uranium is 0.93 µm, and the GSD is 1.48, and the AGR is 0.04 mg/min.

As aforementioned of the generator for producing a narrowly size-distributed aerosol according to the present invention, firstly, the solution from the reservoir is atomized into the first droplets included a predetermined small-sized range of droplets by the atomizer, and then the larger droplets are deposited by using the droplet depositor from the predetermined small-sized range of droplets in the first droplets, and wherein the second droplets are formed by the first droplets, and then a particulate screening and separating means is used to extract the third droplets smaller than the predetermined small-sized range of droplets within the second droplets, and the predetermined small-sized range of droplets can be obtained thereof. Therefore, the aerosol generator can function as a device characterized with the alternative distributions of the narrowly size-distributed aerosol with high concentration in mass, and the liquid or solid aerosol can be generated thereof. The Geometric Standard Deviation (GSD) of the droplet size distribution can be kept under 1.5 and the Mass Median Aerodynamic Diameter (MMAD) is selective so that the user alters the concentration of the solvent from the solution before atomizing. Also, this generator can be operated for more than 8 hours by the self-purification system. The relative GSD with respect to the MMAD, GSD and the Aerosol Generation Rate (AGR) can be maintained under 10% for 8 hours.

While this invention has been described in connection with what is presently considered to be the most practical and preferred embodiment, it is to be understood that the invention is not limited to the disclosed embodiments, but, on the contrary, is intended to cover various modifications and equivalent arrangements included within the spirit and scope of the appended claims.

What is claimed is:

1. A generator for producing a narrowly size-distributed aerosol, comprising:

a reservoir for storing solution and a gas resource utilized by said generator for forming a predetermined small-sized range of droplets from said reservoir;

an atomizer connected to said reservoir, wherein said atomizer atomizes said solution by said generator and forms first droplets including said predetermined small-sized range of droplets;

a droplet depositor provided with an outlet and an inlet installed with said atomizer, wherein said droplet depositor deposits larger sized droplets from said predetermined small-sized range of droplets in said first droplets, and wherein second droplets are formed from said first droplets and passed out through said outlet of said droplet depositor; and a particulate screening and separating means installed on said outlet of said droplet depositor, wherein said particulate screening and separating means is used to extract third droplets smaller than said predetermined small-sized range of droplets within said second droplets, and said predetermined small-sized range of droplets is obtained therefrom.

2. The generator for producing a narrowly size-distributed aerosol according to claim 1, wherein a return pipe is installed between said atomizer and said droplet depositor.

3. The generator for producing a narrowly size-distributed aerosol according to claim 1, wherein said gas resource is air.

4. The generator for producing a narrowly size-distributed aerosol according to claim 1, wherein said particulate screening and separating means comprises:

a cylindrical body provided with a first opening and a second opening, wherein said first opening is connected to said outlet of said droplet depositor for conducting said second droplets therein;

a jet nozzle mounted in said first opening of said cylindrical body for accelerating said second droplets and a nozzle orifice is provided thereon; and a collecting pipe installed in said first opening of said cylindrical body and a collecting opening is provided thereon, wherein said collecting opening spaced with a presetting distance opposite to said nozzle orifice of said jet nozzle is used to collect said predetermined small-sized range of droplets, and said second opening of said cylindrical body is used to conduct said third droplets.

5. The generator for producing a narrowly size-distributed aerosol according to claim 4, wherein said gas resource is conducted into said jet nozzle by pipes.

6. The generator for producing a narrowly size-distributed aerosol according to claim 5, wherein said pipes have a gas flow control means installed therein.

7. The generator for producing a narrowly size-distributed aerosol according to claim 6, wherein said gas flow control means comprises a floating flow meter and a needle valve.

8. The generator for producing a narrowly size-distributed aerosol according to claim 7, wherein said third droplets are drawn by an air intake flow control device.

9. The generator for producing a narrowly size-distributed aerosol according to claim 8, wherein said air intake flow control device comprises a microporous flow meter, a pressure differential, a filter, a needle valve and a vacuum pump.

10. The generator for producing a narrowly size-distributed aerosol according to claim 1, wherein said droplet depositor is a diversion pipe.

11. The generator for producing a narrowly size-distributed aerosol according to claim 10, wherein said diversion pipe comprises at least one bend therein.

12. The generator for producing a narrowly size-distributed aerosol according to claim 11, wherein said diversion pipe generally is L-shaped.

13. The generator for producing a narrowly size-distributed aerosol according to claim 12, wherein said L-shaped diversion pipe is arranged at approximately 7 degrees with respect to the horizontal line from the inlet to the bend thereof.

14. The generator for producing a narrowly size-distributed aerosol according to claim 1, wherein said atomizer is a nebulizing nozzle that includes a low-pressure venturi effect by said gas resource and therefore said solution is drawn from said reservoir; and at the same time, said solution can be atomized into said first droplets with a broad range of particle radius by a centrifugal vortex motion.

15. The generator for producing a narrowly size-distributed aerosol according to claim 14, wherein a pressure regulator is installed between said nebulizing nozzle and said gas resource, and also said pressure regulator is used to control the gas fed into said nebulizing nozzle.

16. The generator for producing a narrowly size-distributed aerosol according to claim 11, wherein said atomizer is a nebulizing nozzle inducing a low-pressure venturi effect by said gas resource and therefore said solution is drawn from said reservoir; while at the same time said solution can be atomized into said first droplets with a broad range of particle radius by a centrifugal vortex motion.

17. The generator for producing a narrowly size-distributed aerosol according to claim 16, wherein an pressure regulator is installed between said nebulizing nozzle and said gas resource, and also said pressure regulator is used to control the gas fed into said nebulizing nozzle.

* * * * *